United States Patent [19]

Sonnett et al.

[11] Patent Number: 5,490,722
[45] Date of Patent: Feb. 13, 1996

[54] HANDS FREE DENTAL FLOSS DISPENSER

[75] Inventors: Gary J. Sonnett; Frederick V. Sprouse, both of Frisco; David L. Hector, Englewood; Robert G. Lowry, Englewood; Bradley M. Woodworth, Englewood, all of Colo.

[73] Assignee: Sprouse and Sonnett, Inc., Frisco, Colo.

[21] Appl. No.: 275,114

[22] Filed: Jul. 14, 1994

[51] Int. Cl.⁶ .................................................. A47B 83/00
[52] U.S. Cl. .............................. 312/237; 225/44; 225/46; 225/51; 206/63.5
[58] Field of Search ............................. 312/34.19, 237; 225/46, 51, 44; 206/63.5

[56] References Cited

U.S. PATENT DOCUMENTS

| | | | |
|---|---|---|---|
| 1,455,673 | 5/1923 | Shalek | 242/138 |
| 2,645,543 | 7/1953 | Mancini | 312/34.19 |
| 3,246,815 | 4/1966 | Aronson | 225/44 |
| 4,088,276 | 5/1978 | Littleton | 225/46 |
| 4,592,669 | 6/1986 | Loase et al. | 225/51 |
| 5,016,661 | 5/1991 | Israel et al. | 132/324 |
| 5,188,133 | 2/1993 | Romanus | 132/325 |
| 5,224,502 | 7/1993 | Walker, Jr. | 132/325 |
| 5,246,022 | 9/1993 | Israel et al. | 132/324 |

*Primary Examiner*—James R. Brittain
*Assistant Examiner*—Gerald A. Anderson
*Attorney, Agent, or Firm*—Gifford, Krass, Groh, Sprinkle, Patmore, Anderson & Citkowski

[57] ABSTRACT

A manually powered hygienic dental floss dispenser enclosed in a housing. A user pulls a lever connected to a first drive belt engaging a free wheel and an inner ratchet wheel, causing the wheels to rotate clockwise. When the user releases the lever, a spring pushes the lever back toward its original position, causing the inner ratchet wheel to engage an outer ratchet wheel engaged with a second drive belt and a daisy wheel. Counterclockwise rotations of the wheels cause the daisy wheel to engage and advance a string of dental floss at pairs of opposing radial extensions of the daisy wheel. When the lever reaches its original position it activates a cutting mechanism that severs the string of dental floss at a measured length. The measured length of dental floss passes from the interior to the exterior of the housing through a feed tube.

18 Claims, 4 Drawing Sheets

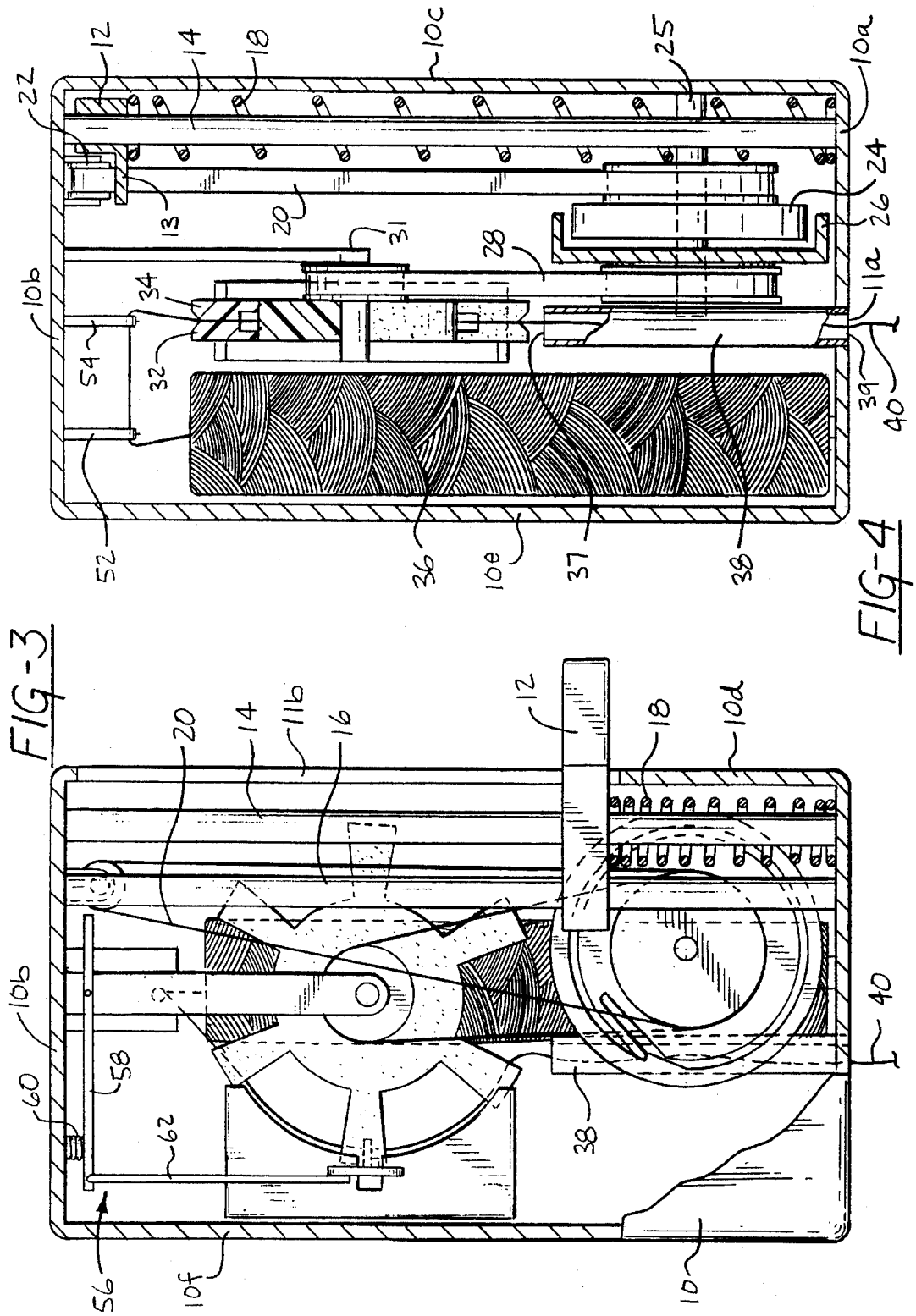

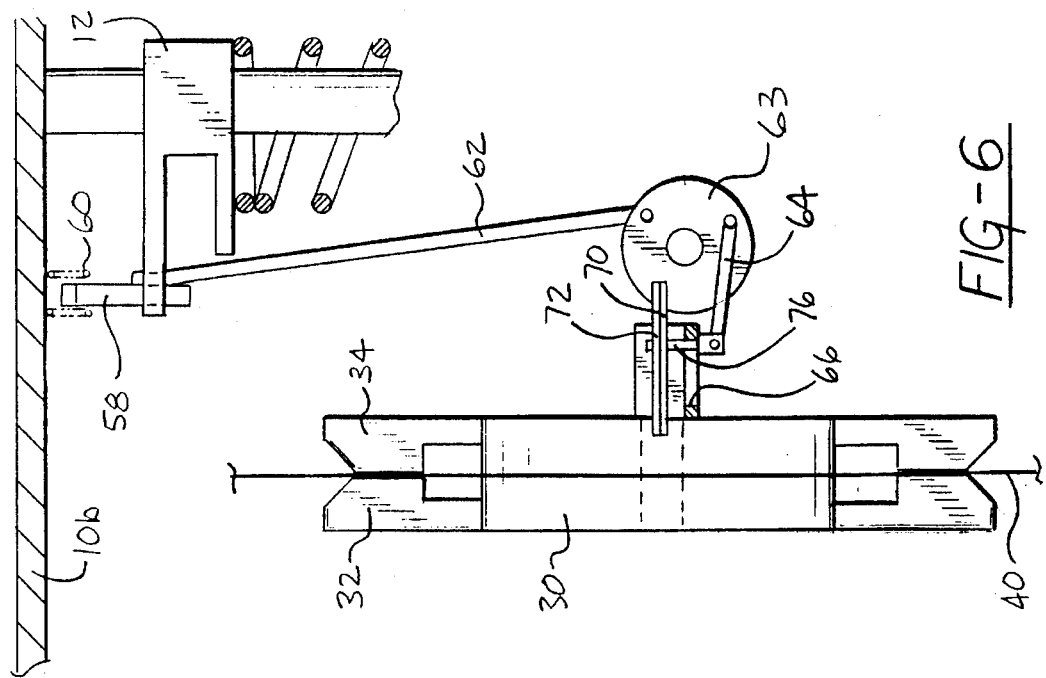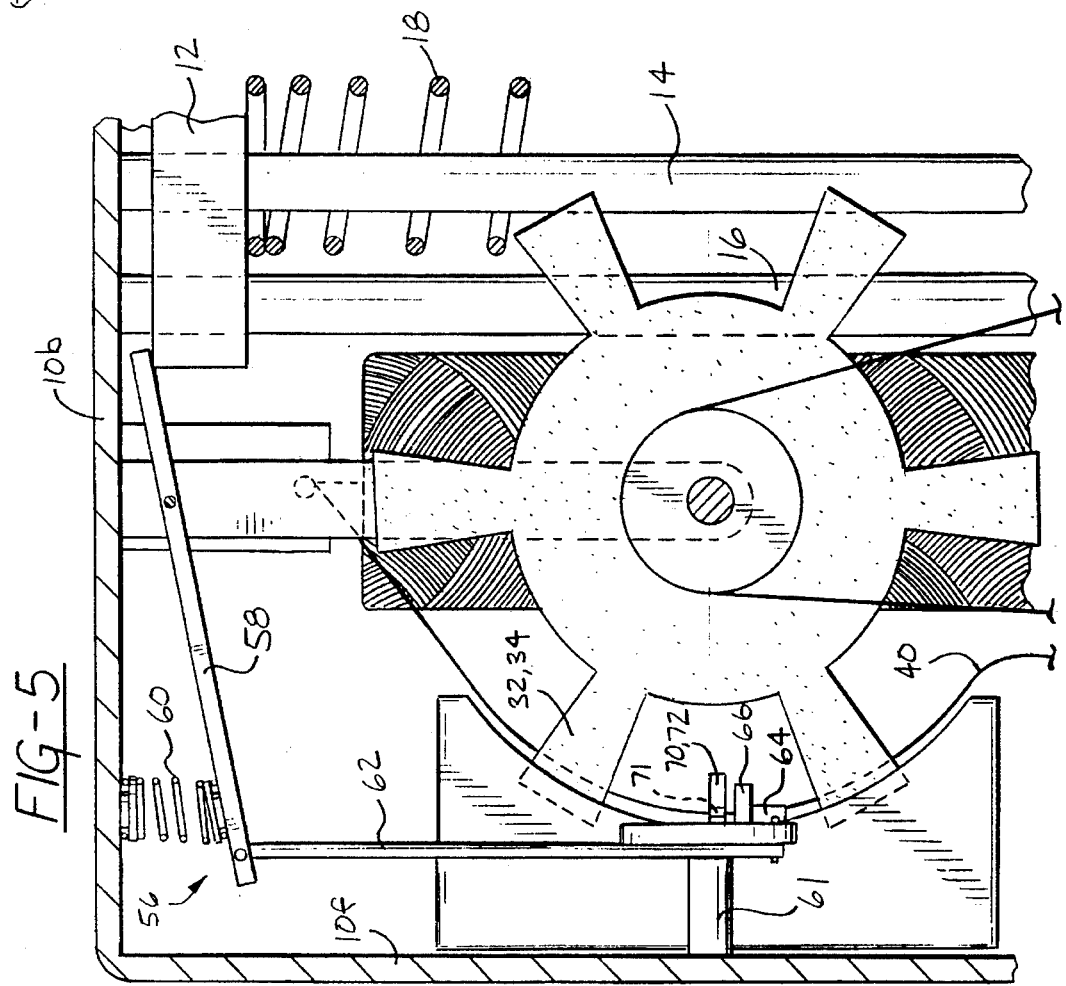

HANDS FREE DENTAL FLOSS DISPENSER

FIELD OF THE INVENTION

This invention relates generally to a dental floss dispenser and, more specifically, to a wall mounted dispenser for dispensing measured lengths of dental floss in a neat and hygienic manner.

BACKGROUND OF THE INVENTION

It is well known that dentists and oral hygienists strongly recommend flossing as a supplement to brushing to remove plaque and other food particles from teeth. Many people do not floss as often as they should due to the inconvenience of carrying dental floss dispensers and the lack of dental floss dispensers in public washrooms. Restauranteurs and operators of service stations with public washroom facilities are concerned with keeping their washrooms clean. Patrons would benefit from being able to use dental floss dispensers in the washrooms, but they want to be assured that the dental floss is supplied in a hygienic manner.

Advances in the art of dental floss dispensers have been limited to the provision of dispensers for dental floss supplied on spools or in various shaped commercially available containers. Little has been done to provide dental floss dispensers suitable for mounting in public washroom facilities and other commercial environments. With conventional dental floss dispensers users are free to choose any desired length of dental floss, which usually results in unnecessary waste. Since severing dental floss from existing dispensers still involves the manual steps of passing the floss over a small hook and jerking the floss against the hook, a portion of unused dental floss can be contaminated each time the dispenser is used. It would be desirable to provide a dental floss dispenser that is convenient, safe and easy to use in commercial environments.

SUMMARY OF THE INVENTION

It is the principal object of the present invention to provide a dental floss dispenser that delivers dental floss in such a manner that unused dental floss will not be contaminated by human hands. Such a dispenser could be mounted in public washroom facilities, dentist and oral hygienist's offices, and even washrooms in homes. It is a further object of the present invention to minimize waste of dental floss by providing a cutting means within the dispenser that automatically severs the dental floss at measured lengths.

A floss dispenser formed in accordance with the present invention includes a spool of dental floss and means for dispensing measured lengths of the dental floss. The dispensing means is manually powered by a user moving a lever between extreme positions against a spring bias. When the lever returns to its initial position, a cutting mechanism severs a measured length of the dental floss that the user may then use to clean his or her teeth. In the preferred embodiment, the dental floss dispenser is enclosed in a housing and has a manually powered means for engaging a free end of dental floss wound on a spool of dental floss and moving the dental floss from inside the housing to outside the housing. After a user pulls and releases a lever, a spring returns the lever to its original position. Once the lever reaches its original position, a cutting mechanism made up of a system of links, a wheel, and a pair of scissors engages the dental floss and severs the floss into a measured length. The floss dispenser may typically include a lever, a housing, a first drive belt fixed to the lever and engaging a free wheel and an inner ratchet wheel, a second drive belt engaging a portion of an outer ratchet wheel and a daisy wheel, and a feed tube for passing dental floss from the interior of the housing to the exterior of the housing. The daisy wheel includes pairs of opposing radial finger-like extensions for engaging dental floss. There may also be a clamping means for pushing the opposing radial extensions toward one another to grip the dental floss.

BRIEF DESCRIPTION OF THE DRAWINGS

FIG. 3 is a front plan view of a preferred embodiment of the dental floss dispenser, showing the pull handle at its lowermost position, with the housing cut away for clarity;

FIG. 4 is a partially segmented side plan view of the dental floss dispenser;

FIG. 5 is an enlarged front plan view, partially broken away, of a preferred embodiment of the dental floss dispenser;

FIG. 6 is an enlarged side plan view of the cutting mechanism of dental floss dispenser before being triggered by the lever returning to its uppermost position;

DETAILED DESCRIPTION OF THE PREFERRED EMBODIMENT

Figure 2:
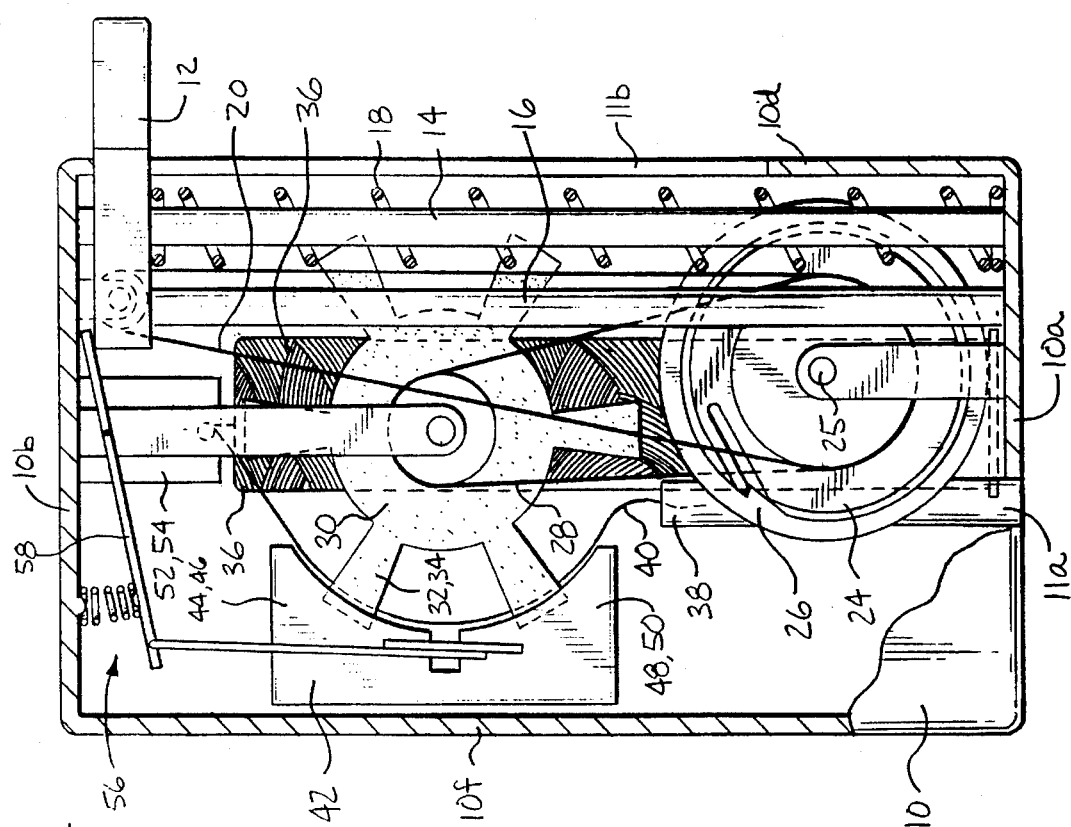
FIG. 2 is a front plan view of a preferred embodiment of the dental floss dispenser, showing the pull handle at its uppermost position, with the housing cut away for clarity.
Figure 1:
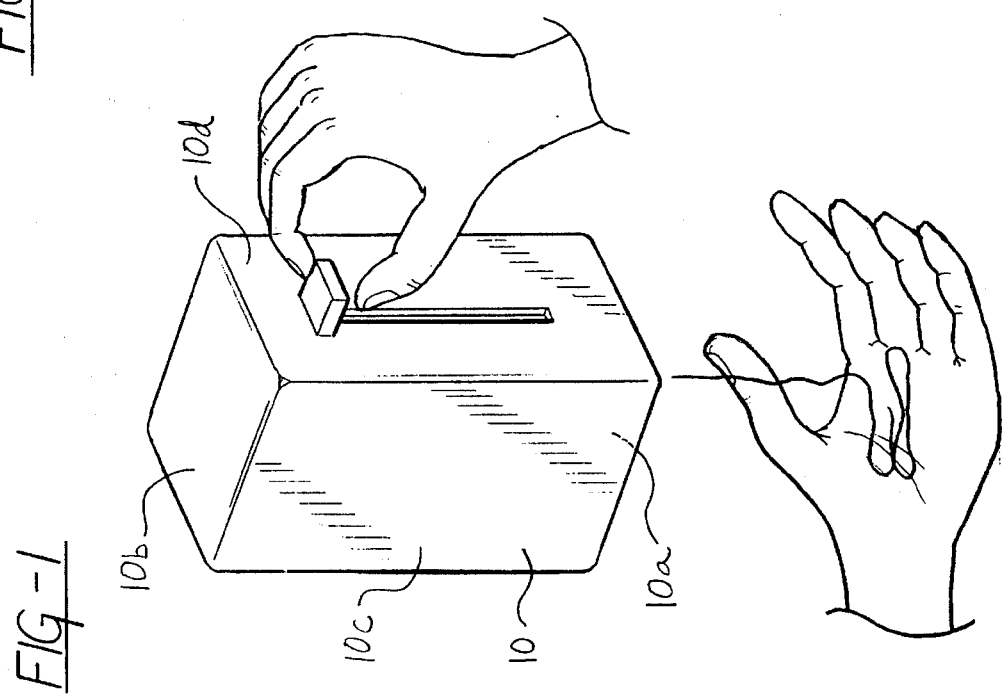
FIG. 1 is a perspective view of a preferred embodiment of the dental floss dispenser.
Figure 8:
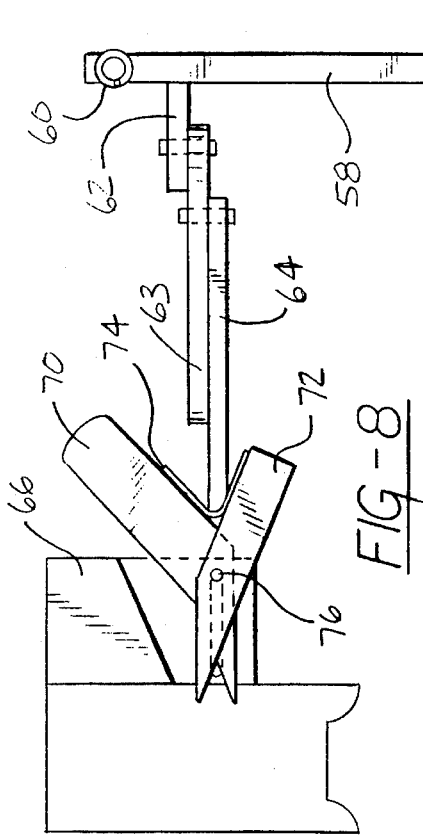
FIG. 8 is an enlarged top plan view of the cutting mechanism of the dental floss dispenser before being triggered by the lever.
Figure 9:
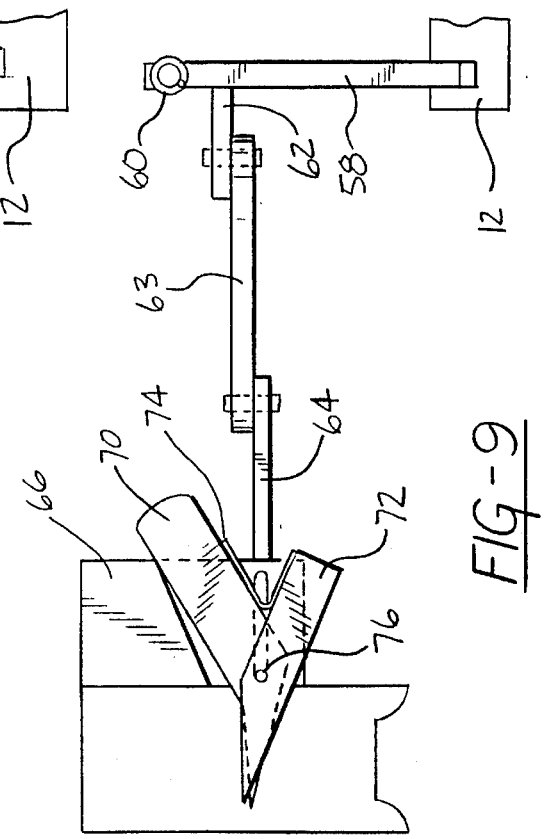
FIG. 9 is an enlarged top plan view of the cutting mechanism of the dental floss dispenser after being triggered by the lever.
Figure 7:
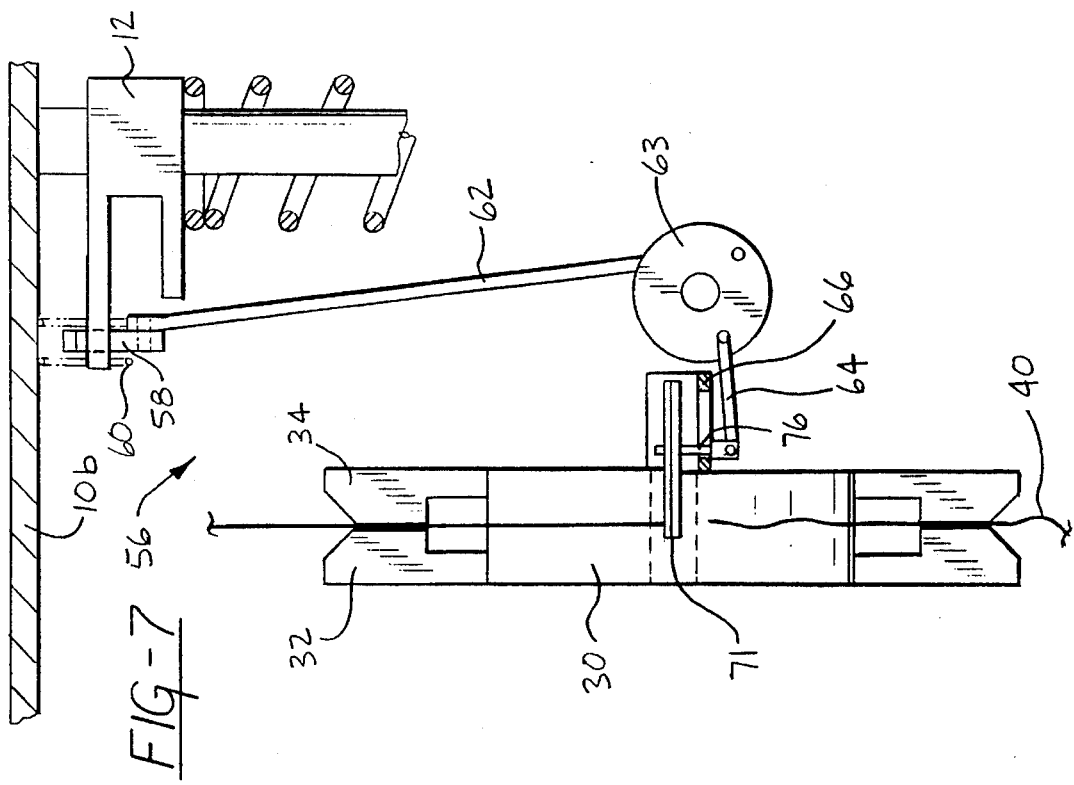
FIG. 7 is an enlarged side plan view of the cutting mechanism of the dental floss dispenser after being triggered by the lever returning to its uppermost position.

The present invention includes a dental floss dispenser enclosed in a housing 10. The housing 10 may be mounted on a vertical wall at a comfortable height for the average user. The housing 10 has a bottom 10a, a top 10b, a side walls 10c, 10d, 10e, 10f, an opening 11a in the bottom of the housing 10a allowing dental floss to pass from inside the housing to outside the housing, and a slot 11b in one side wall 10d. Slot 11b allows a lever 12 to move vertically along shafts 14 and 16 extending between the bottom of the housing 10a and the top of the housing 10b from an uppermost position as shown in FIG. 2 to a lowermost position as shown in FIG. 3. A spring 18 surrounding the shaft 14 compresses as the lever is displaced from its uppermost position to its lowermost position. The shaft 14 prevents the spring 18 from buckling and ensures that the spring 18 will push the lever 12 back toward its uppermost position when the lever is released.

As can be seen in FIG. 4, the lever is attached at 13 to a first drive belt 20 that engages both a free wheel 22 and a portion of an inner ratchet wheel 24. The inner ratchet wheel 24 is coaxially supported with an outer ratchet wheel 26 by a ratchet wheel support shaft 25. The lever may be attached to the first drive belt 20 by various means including but not limited to a clamp, staple, screw or by a strong adhesive. As the lever 12 is pulled from its uppermost position to its lowermost position, the first drive belt 20 causes the inner ratchet wheel 24 to rotate in a clockwise direction approximately 365°. Upon completing its clockwise rotation, the inner ratchet wheel 24 is in a position to engage the outer ratchet wheel 26. The clockwise rotation for a full displacement of the lever 12 is preferably greater than 360° to ensure the inner ratchet wheel 24 will engage the outer ratchet wheel 26 even if a user releases the lever just before reaching its lowermost position.

A second drive belt 28 engages both a portion of the outer ratchet wheel 26 and a portion of a daisy wheel 30. The daisy wheel 30 is axially supported by a daisy wheel support shaft 31. The daisy wheel 30 includes a plurality of pairs of opposing radial finger-like extensions 32,34 for engaging dental floss 40. When the lever 12 is released from its lowermost position, spring 18 pushes the lever upward, causing the first drive belt 20 to rotate both the inner ratchet wheel 24 and the outer ratchet wheel 26 in a counterclockwise direction. The second drive belt 28 simultaneously rotates the daisy wheel 30 in a counterclockwise direction.

As shown in FIG. 4, dental floss wound on a spool 36, is fed through a plurality of floss guides 52,54 and picked up by pairs of radial opposing extensions 32,34 of the daily wheel. Rotation of the daisy wheel causes movement of the dental floss. The spool 36 may, but need not necessarily rotate within the housing while dental floss is moving through the floss guides and around the daisy wheel. Dental floss wound on a non-rotating spool could still be removed if pulled substantially vertically off the spool. It is recognized that balls, bobbins, or wheels of dental floss may be used for the spool of dental floss in the present invention. As the daisy wheel rotates in a counterclockwise direction, each pair of radial opposing extensions passes between jaws 44,46 of a clamp 42. The jaws 44 and 46 push the opposing radial extensions of the daisy wheel toward one another, causing the radial opposing extensions 32 and 34 to grip of dental floss 40. It is recognized that other embodiments may use different means for engaging and advancing dental floss, such as having a belt with a plurality of pairs of finger-like extensions on the outer surface or side surfaces of the belt for engaging the dental floss.

As illustrated in FIGS. 5–9, when the lever returns to its uppermost position, a cutting mechanism 56 is triggered that severs the dental floss at a point 71 between jaws 44,46 of clamp 42 and jaws 48,50 of clamp 42. A finger-like extension (not shown) directs the dental floss 40 off the radial opposing extensions 32,34 of the daisy wheel 30 and into the proximal end 37 of a feed tube 38 that guides the dental floss from the interior of housing 10 to the exterior of the housing at the distal end 39 of the feed tube.

Cutting mechanism 56 includes a toggle member 58, a spring 60, a first linking member 62, a turning wheel 63 axially supported by a turning wheel support shaft 61, a second linking member 64, a cutting stage 66 located on the clamp 42, and a pair of scissors 70,72 connected to second linking member 63 by a pin 76. There is also a spring 74 attached to scissor 70 and abutting scissor 72, or alternatively attached to scissor 72 and abutting scissor 70, that acts so as to keep the scissors 70,72 in an open position by pushing the scissors apart while the cutting mechanism 56 is not severing dental floss.

When the lever 12 is in its uppermost position, the spring 60 is in a state of tension. When the pull handle is moved downward, spring 60 pulls the toggle member 58 to a horizontal position. First linking member 62 simultaneously rotates the turning wheel 63 counterclockwise such that second linking member 64 pulls the scissors 70,72 away from the dental floss 40. When spring 18 returns the lever to its uppermost position, the toggle member 58 is moved to a slanted position, causing first linking member 62 to rotate the turning wheel 63 clockwise such that second linking member 64 causes scissors 70,72 to engage and sever the dental floss 40.

As an alternative to pin 76, second linking member 64 may abut scissor 70 or scissor 72. In such an embodiment, second linking member 64 pushes scissors 70 and 72 toward the dental floss 40 while the turning wheel 63 rotates in a clockwise direction. When the lever is moved downward, spring 74 forces second linking member 64 back toward turning wheel 63 as it pushes the scissors apart, in cooperation with spring 63, rotating the turning wheel counterclockwise and returning the toggle member 58 to its horizontal position.

In the preferred embodiment, cutting mechanism 56 severs the dental floss into a measured length while the dental floss is still engaged by opposing radial extensions 32 and 34 of the daisy wheel. In other embodiments the cutting mechanism may sever the dental floss at a point adjacent to the feed tube 38 in the interior of the housing. Alternatively, conventional cutting means may be used, for example, providing a hook located at the distal end 39 of the feed tube on the exterior of the housing 38. A user would then wrap a dispensed length of dental floss around the hook and manually sever the length of floss from the dispenser.

It is recognized that the length of dental floss dispensed may be controlled, for example, by varying the ratio between the radii of the portions of the outer ratchet wheel 26 and the daisy wheel 30 that engage the second drive belt 28. This varies the number of revolutions the daisy wheel makes for each counterclockwise revolution of the inner and outer ratchet wheels. The length of dental floss may also be controlled by varying the distance R between the center of the daisy wheel 30 and the positions on the daisy wheel at which the dental floss is engaged by the pairs of opposing radial extensions 32,34 of the daisy wheel. If the portion of the outer ratchet wheel 26 that engages the second drive belt 28 has a radius approximately twice the radius of the portion of the daisy wheel that engages the second drive belt, the daisy wheel 30 will make approximately two revolutions during the time the lever returns to its uppermost position. The length of dental floss dispensed would then be approximately equal to $4\pi R$.

In other embodiments, the ratio of the radii of the free wheel 22 and the portion inner ratchet wheel 24 that engages the first drive belt 20 may be such that the inner ratchet wheel makes one clockwise revolution when the lever 12 is pulled half-way between its uppermost position and its lowermost position and two clockwise revolutions when the lever is pulled to its lowermost position. This arrangement gives a user the choice of a shorter or a longer length of dental floss.

The housing 10 should have an access means for resupplying dental floss to the dispenser and fixing dental floss entanglements. Additionally, the housing could have an aperture for a receptacle in the dispenser for users to dispose of used lengths of dental floss.

It should be noted that the preferred embodiment is merely exemplary and additional embodiments which are not illustrated above are intended to be within the scope of the present invention.

We claim:

1. Apparatus for dispensing measured lengths of dental floss comprising:

a housing;

a spool disposed inside the housing having a length of dental floss wound thereon;

a dispensing means for engaging a free end of the length of dental floss at a position inside the housing and moving the free end of the length of dental floss a measured distance to a position outside the housing where the free end of the length of dental floss may be grasped by a user; and a cutting means for severing the length of dental floss after the dispensing means has moved the free end of the length of dental floss the measured distance.

2. The apparatus of claim 1 wherein the dispensing means is manually powered by a user moving a lever between a first position and a second position against a spring bias.

3. The apparatus of claim 2 wherein the housing includes an opening allowing dental floss to pass from inside the housing to outside the housing and a slot allowing the lever to extend from inside the housing to outside the housing and to move between the first position and the second position.

4. The apparatus of claim 3 wherein the dispensing means further periodically engages the length of dental floss at points along the length of dental floss and includes moving the free end of the length of dental floss toward the opening in the housing that allows dental floss to pass from inside the housing to outside the housing.

5. The apparatus of claim 4 wherein the dispensing means includes a movable engaging mechanism comprising a movable base having a plurality of pairs of opposing extensions, the pairs of opposing extensions capable of engaging dental floss.

6. The apparatus of claim 5 wherein the dispensing means further includes a clamping means for pushing the opposing extensions of the movable base toward one another and into close communication with dental floss.

7. The apparatus of claim 5 wherein the dispensing means further includes a drive belt system driven by a user manually moving the lever from the first position to the second position against the spring bias and the spring returning the lever to the first position.

8. The apparatus of claim 7 wherein the movable base having the plurality of pairs of opposing extensions is a wheel driven by the drive belt system.

9. The apparatus of claim 7 wherein the drive belt system comprises:

a first drive belt connected to the driving member;

a free wheel in driven association with the first drive belt;

a primary ratchet wheel in driven association with the first drive belt;

a second drive belt in driving association with the movable base; and a secondary ratchet wheel in driving association with the second drive belt and periodically engaged by the primary ratchet wheel.

10. An apparatus for dispensing measured lengths of dental floss comprising:

a housing;

a spool disposed inside the housing having a length of dental floss wound thereon;

a lever extending from the inside the housing to outside the housing and movable between a first position and a second position;

a spring biasing the lever toward the first position and disposed within the housing;

a first drive belt disposed within the housing connected to the driving member;

a free wheel in driven association with the first drive belt;

an inner ratchet wheel in driven association with the first drive belt;

an outer ratchet wheel periodically engaged by the inner ratchet wheel;

a daisy wheel having a plurality of pairs of opposing radial extensions for periodically engaging and carrying a free end of dental floss from the length of dental floss;

a second drive belt in driven association with the outer ratchet wheel and in driving association with the daisy wheel; and a cutting means.

11. The apparatus of claim 10 further comprising a clamping means inside the housing for pushing opposing radial extensions of the daisy wheel toward one another.

12. The apparatus of claim 10 wherein the cutting means comprises:

a toggle member having a spring biasing the toggle member toward a first orientation, the toggle member moving to a second orientation when the driving member returns to the first position;

a first linking member connected to the toggle member and to a wheel, the first linking member causing the wheel to rotate when the toggle member moves from the first orientation to the second orientation;

and a second linking member connected to the wheel and in communication with a first scissor, the second linking member causing the first scissor to move toward a second scissor and into close communication with dental floss engaged by a plurality of pairs of radial extensions of the daisy wheel when the wheel turns, whereby the length of dental floss is severed.

13. The apparatus of claim 10 further comprising a feed tube extending from a proximal end in the interior of the housing to a distal end on the exterior of the housing capable of receiving and delivering dental floss from the pairs of opposing radial extensions of the daisy wheel.

14. The apparatus of claim 13 further comprising a finger-like projection at the proximal end of the feed tube for directing dental floss away from the pairs of opposing radial extensions of the daisy wheel and into the proximal end of the feed tube.

15. The apparatus of claim 13 wherein the cutting means is a manual cutting means including a hook provided near the distal end of the feed tube on the exterior of the housing.

16. The apparatus of claim 10 further comprising a plurality of floss guides located within the housing to prevent tangling of dental floss.

17. The apparatus of claim 10 further comprising a receptacle inside the housing to receive used lengths of dental floss.

18. The apparatus of claim 10 further comprising a means for access to the inside of the housing, whereby dental floss can be resupplied and dental floss tangles can be repaired.

* * * * *